United States Patent [19]

Singleton

[11] Patent Number: 4,472,525

[45] Date of Patent: Sep. 18, 1984

[54] ETHYLENE OLIGOMERIZATION PROCESS

[75] Inventor: David M. Singleton, Seabrook, Tex.

[73] Assignee: Shell Oil Company, Houston, Tex.

[21] Appl. No.: 501,582

[22] Filed: Jun. 6, 1983

[51] Int. Cl.³ .............................................. B01J 31/12
[52] U.S. Cl. ..................................... 502/155; 585/527
[58] Field of Search ................................ 502/155, 162

[56] References Cited

U.S. PATENT DOCUMENTS

| | | | |
|---|---|---|---|
| 3,131,155 | 4/1964 | Luttinger | 502/162 X |
| 3,379,706 | 4/1968 | Wilke | 502/162 X |
| 3,535,397 | 10/1970 | Schott | 502/155 X |
| 3,644,563 | 2/1972 | Bauer et al. | 502/162 X |
| 3,676,523 | 7/1972 | Mason | 502/162 X |
| 3,686,159 | 8/1972 | Bauer et al. | 502/155 X |
| 3,907,850 | 9/1975 | Capra et al. | 502/162 X |

*Primary Examiner*—Patrick Garvin

[57] ABSTRACT

Ethylene is oligomerized to a mixture of olefinic products of high linearity in the presence of a catalyst comprising an atom of nickel in complex with an olefinically unsaturated compound and an o-dihydrocarbylphosphinophenyl alcohol or lower alkyl ether ligand.

13 Claims, No Drawings

ETHYLENE OLIGOMERIZATION PROCESS

FIELD OF THE INVENTION

This invention relates to a process for the oligomerization of ethylene to a mixture of olefinic product having high linearity by using a catalyst comprising (a) a nickel compound comprising an atom of nickel in complex with a olefinically unsaturated compound and (b) an o-dihydrocarbylphosphinophenol. The instant invention also relates to the novel catalysts utilized herein.

BACKGROUND OF THE INVENTION

The present invention relates to the production of a mixture of olefinic products which are substantially alpha-olefins and which have a high degree of linearity. Such olefins comprise for example, those of the plasticizer range, i.e., $C_4$–$C_{10}$, those of the detergent range, i.e., $C_{12}$–$C_{20}$ and higher olefins, e.g., polyethylene. The lower molecular weight olefins can be converted to sulfonates or alcohols by known commercial processes. The $C_{12}$–$C_{20}$ olefins find use in the detergent-products area. Lower molecular weight alcohols can be esterified with polyhydric acids, e.g., phthalic acid to form plasticizers for polyvinylchloride.

The use of o-dihydrocarbylphosphenobenzoic acid as a ligand to be combined with a nickel salt which product is used as an oligomerization catalyst is known in the art. See for example U.S. Pat. No. 3,676,523, issued July 11, 1972. The use of a dihydrocarbylphosphinophenol alcohol or lower alkyl ether rather than a dihydrocarbylphosphenobenzoic acid provides an entirely new class of ligands to be utilized with a catalyst for the oligomerization of ethylene. The phenol/ether ligand is not subject to decarboxylation during reaction processes as is the benzoic acid ligand. The phenol/ether ligand also provides a different olefin distribution than the benzoic acid ligand, thus allowing for the production of alpha-olefins having a different carbon number distribution than those produced using the benzoic acid ligand.

SUMMARY OF THE INVENTION

The instant invention comprises a process for oligomerizing ethylene to a mixture of olefinic products comprising a large proportion of alpha-olefins having high linearity by reacting the ethylene in liquid phase solution in the presence of a catalyst composition comprising (a) a nickel compound comprising an atom of nickel in complex with an olefinically unsaturated compound and (b) an o-dihydrocarbylphosphinophenyl alcohol and/or lower alkyl ether ligand. The process is characterized by an ethylene conversion to an alpha-olefin product mixture wherein said alpha-olefins have a high degree of linearity.

DESCRIPTION OF THE PREFERRED EMBODIMENTS

The catalysts of the present invention are described as the product of the reaction of a nickel compound comprising an atom of nickel in complex with an olefinically unsaturated compound, preferably biscyclooctadiene-1,5-nickel (O), with an o-dihydrocarbylphosphinophenyl alcohol and/or lower alkyl ether ligand.

The nickel compound employed as a catalyst for the oligomerization process may be described as comprising an atom of nickel from a biscyclooctadiene nickel (O) complex or like complex of nickel (O) or nickel (I) further complexed with an o-dihydrocarbylphosphinophenyl alcohol and/or lower alkyl ether ligand.

Although it is not desired to be bound by any particular theory it appears likely that the catalyst molecule undergoes chemical transformation during the course of the oligomerization reaction possibly involving coordination and/or bonding of ethylene to the nickel moiety. However, it appears likely that the phenol ligand remains complexed and/or chemically bonded to the nickel moiety during the course of the reaction and that this complex of nickel and phenol ligand is the effective catalytic species of the oligomerization process. In any event, the ligand is an essential component of the catalyst and provided the nickel catalyst contains the required phenol/ether ligand, the nickel catalyst may be complexed with a variety of additional organic complexing ligands.

The catalysts of the present invention are typically formed in situ in the reaction medium but the present invention encompasses the nickel-phenol catalysts as described regardless of what sequence is used for catalyst preparation and oligomerization. Whether the catalyst is formed and perhaps even identified prior to its use as an oligomerization catalyst or is formed in the reaction medium while the oligomerization is proceeding, its exact active form during the oligomerization reaction is not precisely ascertainable. For this reason the catalyst is preferably described as the product of the reaction of the nickel compound with the o-dihydrocarbylphosphinophenyl alcohol and/or lower alkyl ether ligand.

When the catalyst is characterized as the product of the reaction of a nickel compound with the phenol/ether ligand wherein the nickel compound is selected from the group consisting of nickel (O) compositions and nickel (I) compositions, the characterization does not encompass nickel which is reducible to a lower positive valence state. In the case of the Ni(I) compositions, the nickel is capable of being reduced to a lower (nonpositive) valence state which is zero (O). The nickel (O) compositions comprise an atom of nickel complexed or chemically bonded to sufficient complexing ligands to satisfy the coordination number of the nickel atom which typically but not invariably is four. However, because of the difficulty in ascribing oxidation states or valences to transition metal-containing catalysts, the catalysts of the present invention are preferably defined in terms of reaction products as above or in terms of an empirical representation as described below rather than in precise bonding or oxidation state terms.

In another manner of describing the catalyst of the present invention, the compositions are represented by the empirical Formula I:

$$L_nNi(Z)_m \qquad (I)$$

wherein Z is o-dihydrocarbylphosphinophenyl alcohol or lower alkyl ether, L is an olefinically unsaturated compound of from 2 to 20 carbon atoms, of up to 4 olefinic linkages, and of up to 3 carbocylic rings, n amd m are selected from numbers of from 1 to 3 and the sum of n and m may be but is not necessarily equal to 4. However, as pointed out above, it is preferred to describe the catalyst as the reaction product of the nickel complex and the phenol ligand and it is to be understood that the composition as depicted in Formula I is meant only to represent the empirical composition and that the precise nature of the bonding between the o-dihydrocarbylphosphinophenyl alcohol or lower alkyl ether ligand and the nickel moiety is not definitely known. However, it is considered likely that the nickel is in a low valence state, e.g. zero-valent or mono-valent nickel, which valence state is dependent on the nature of the chemical bonding between the nickel moiety and the ligand.

The organic complexing ligand L is an olefinically unsaturated compound of from 2 to 20 carbon atoms, of up to 4 olefinic linkages and of up to 3 carbocyclic rings. A particularly preferred class of olefinically unsaturated compounds are olefins of from 2 to 12 carbon atoms, represented by the Formula II:

(II)

wherein R' and R'' independently are hydrogen, alkyl, cycloalkyl, alkenyl, cycloalkenyl, aralkyl, aryl or alkaryl of up to 8 carbon atoms, with the proviso that the R' and R'' groups may together form a divalent aliphatic moiety of from 2 to 10 carbon atoms of up to three additional olefinic double bonds as the sole carbon-carbon unsaturation.

Illustrative olefins of Formula II therefore include ethylene, propylene, 2-butene, 1-pentene, 1-hexene, 1-octene, 1-decene, butadiene, isoprene, 1,3,5-octatriene, 1,3,7-octatriene, cyclopentene, cycloheptene, cyclopentadiene, cyclohexa-1,3-diene, cycloocta-1,5-diene, cyclooctatriene, cyclooctatetraene and cyclododecatriene.

The particularly preferred organic complexing ligand L for this invention is cyclooctadiene. This moiety is unique and gives particularly good results in the oligomerization of ethylene as will be shown later. The cyclooctadiene, in bonding terms, is π-bonded to the nickel as opposed to the sigma bonding between nickel and for instance cyclopentadienyl chelates or at least is bonded to the nickel in a manner different than the chelate bonding between cyclopentadiene and nickel.

The nickel composition employed in the oligomerization process is prepared by a variety of methods. In a preferred method, the catalyst composition is prepared by contacting an olefinic-nickel compound and the phosphino phenol or ether ligand. The preferred class of olefinic-nickel compounds useful as catalyst precursors are zero-nickel compounds represented by the Formula III:

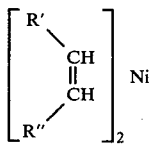
(III)

wherein R'CH=CHR'' has the significance as defined in Formula II. Illustrative nickel compounds of Formula III are therefore biscyclooctadiene nickel (O), biscyclooctatetraene nickel (O), and bis(1,3,7-octatriene) nickel (O).

Another class of olefinic-nickel compounds useful as catalyst precursors is π-allyl nickel compounds wherein the nickel moiety is bonded to a π-allylic moiety characterized by delocalization of the electronic contribution of the π-allyl moiety among three contiguous carbon atoms. One suitable type of π-allyl nickel compounds is represented by the Formula IV:

wherein R' and R'' independently are hydrogen, alkyl, cycloalkyl, alkenyl, cycloalkenyl, aralkyl, aryl or alkaryl of up to 8 carbon atoms, Y is halogen, preferably halogen of atomic number from 17 to 35 inclusive, i.e., chlorine or bromine, alkoxy or alkanoyloxy of up to 10 carbon atoms, and the dotted line designation represents the electronic delocalization among the three illustrated contiguous carbon atoms, with the proviso that R'' together with one R' may form a divalent hydrocarbyl moiety of 2 to 10 carbon atoms, preferably 2 to 5 and of up to 3 additional olefinic double bonds. When considered as a whole, preferred π-allyl moieties have from 3 to 12 carbon atoms and are otherwise free from aliphatic unsaturation unless the π-allyl moiety is part of a closed ring system.

Illustrative of suitable π-allyl nickel halides of the above Formula IV are π-allylnickel chloride, π-allylnickel bromide, π-crotylnickel chloride, π-methylallylnickel chloride, π-ethylallylnickel chloride, π-cyclopentenylnickel bromide, π-cyclooctenylnickel chloride, π-cyclooctadienylnickel chloride, π-cinnamylnickel bromide, π-phenylallylnickel chloride, π-cyclohexenylnickel bromide, π-cyclododecenylnickel chloride and π-cyclododecatrienylnickel chloride. Although the complex of the above Formula IV and other π-allyl nickel halides probably exist independently in the form of a dimer, for convenience and simplicity the π-allyl nickel halides are herein depicted and named as monomeric species.

Other suitable π-allyl nickel compounds of Formula IV are π-allylnickel acetate, π-methylallylnickelpropionate, π-cyclooctenylnickel octoate, π-allylnickel methoxyate and π-allylnickel ethoxyate.

Another suitable type of π-allyl nickel compounds useful as catalyst precursors is bis-π-allyl nickel compounds represented by Formula V:

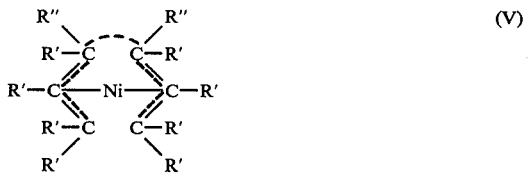

wherein R'', R' and the dotted line designation have the same significance as defined in Formula IV with the proviso that R'' together with one R' of the same π-allylic moiety may form a divalent alkylene moiety of 2 to 10 carbon atoms, preferably of 2 to 5. When considered as a whole, preferred π-allyl moieties have from 3 to 12 carbon atoms and are otherwise free from aliphatic unsaturation unless the allyl moiety is part of a closed ring system. Illustrative of suitable bis-π-allyl nickel compounds of the above Formula V are bis-π-allyl nickel, bis-π-methallyl nickel, bis-π-cinnamylnickel, bis-π-octadienylnickel, bis-π-cyclohexenylnickel, π-allyl-π-methallylnickel, and bis-π-cyclooctatrienylnickel.

The o-dihydrocarbylphosphinophenyl alcohol and lower alkyl ether ligands employed in the preparation of the catalyst composition of the invention generally have from eight to 30 carbon atoms, but preferably from 14 to 20 carbon atoms, and are represented by the formula VI:

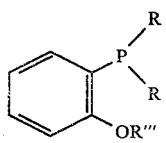

wherein R is a monovalent hydrocarbyl group and R''' is hydrogen or lower alkyl of carbon number 1 to about 6.

Illustrative of suitable R groups are hydrocarbon alkyl R groups such as methyl, ethyl, isobutyl, lauryl, stearyl, cyclohexyl, and cyclopentyl; hydrocarbon alkyl or alkenyl R groups having aromatic substituents such as benzyl, phenylcyclohexyl and phenylbutenyl, and aromatic R groups such as phenyl, tolyl, xylyl and p-ethylphenyl. Preferred R groups are alicyclic or aromatic groups of six to ten carbon atoms, especially phenyl and cycloalkyl of five to ten carbon atoms, especially cyclohexyl.

Illustrative o-dihydrocarbylphosphinophenol ligands of formula VI are o-diphenylphosphinophenol, o-(methylphenylphosphino)phenol, o-(ethyltolylphosphino)phenol, o-dicyclohexylphosphinophenol, o-(cyclohexylphenylphosphino)phenol and o-dipentylphosphinophenol.

Preferred phenol ligands of Formula VI are those wherein the R groups are aromatic or cycloalkyl of six to ten carbon atoms, particularly diarylphosphinophenols and arylcycloalkylphosphinophenols. Such aryl- and cycloalkyl-substituted phosphinophenol ligands are preferred largely because catalyst compositions prepared therefrom catalyze the oligomerization of ethylene to a product mixture containing a high proportion of oligomers in the useful $C_4$–$C_{10}$ and $C_{12}$–$C_{20}$ carbon ranges.

A most preferred ligand is o-diphenylphosphinophenol. This ligand can be prepared by methods readily available in the art. For example, see Rauchfuss, *Inorganic Chemistry*, volume 16, number 11, pp. 2966–2968, 1977.

Illustrative of suitable ether compounds would be the lower alkyl ether analogs of the phenol compounds described above, such as, for example, o-dihydrocarbylphosphinophenylmethyl ether, o-dihydrocarbylphosphinophenylethyl ether, o-dihydrocarbylphosphinophenylpropyl ether and the like. The lower alkyl moiety of the ether has a carbon number ranging from 1 to about 6. The methyl moiety is a preferred lower alkyl species. The most preferred ether ligand is o-diphenylphosphinophenylmethyl ether.

The exact form the ether ligand takes in forming a complex with nickel is not known. It is possible that the lower alkyl ether complex is converted in part into the alcohol complex under reaction conditions. It has been noted that for platinum complexes of o-diphenylphosphinophenylmethyl ether ligand, heating to about 270° C. caused dimethylation and formation of the phenol complex (C. E. Jones, B. L. Shaw and B. L. Turtle: J. Chem. Soc., Dalton Trans. (1974) 992).

The catalyst composition is suitably preformed by contacting the catalyst precursors in an inert diluent, e.g., diluents employed for the oligomerization process. In another modification, however, the catalyst precursor components are contacted in the presence of the ethylene reactant during the initiation of the oligomerization process. By any modification, the catalyst precursor components are contacted at temperatures from about 25° C. to 100° C. In the reaction, the ratio of nickel component to phenol/ether ligand can be between 0.5:1 to 1:12 with a preferred range of 1:1 to 1:4.

The nickel catalyst is suitably employed as an unsupported material. In certain modifications, the nickel catalyst can be supported on a catalyst carrier which is normally solid under reaction conditions and is heterogeneous, i.e., is substantially insoluble in the reaction medium. Illustrative of suitable inorganic, solid catalyst carriers are inorganic acidic oxides such as alumina and inorganic materials known as refractory oxides. Suitable refractory oxides include synthetic components as well as acid treated clays and similar materials such as kieselguhr or crystalline macroreticular aluminosilicates known in the art as molecular sieves. In general, synthetic catalyst carriers are preferred over natural occurring materials or molecular sieves. Exemplary synthetic refractory catalyst carriers include alumina, silica-alumina, silica-magnesia, silica-alumina-titania, silica-alumina-zirconia, silica-titania-zirconia, silica-magnesia-alumina and the like. As for organic supports, subitably functionalized polystyrene, and polystyrene-divinylbenzene supports would be suitable.

When the catalyst composition is supported, the proportion of catalyst composition to carrier is not critical. In general, proportions of catalyst composition from about 0.01% to about 70% by weight, based on the catalyst carrier are satisfactory, with amounts of from about 0.1% to about 20% by weight, calculated on the same basis, being preferred. The catalyst composition is introduced onto the carrier in any suitable manner. In one modification, the supported catalyst composition is prepared by intimately contacting the performed catalyst composition and the carrier in an inert diluent, preferably the same inert diluent employed for preparing the catalyst composition. In another modification, the catalyst compositions can be prepared directly on the catalyst carrier support surface by contacting the catalyst composition precursors in the presence of the catalyst carrier in a suitable inert diluent.

The amount of catalyst composition employed in the oligomerization process is not critical. In general, amounts of catalyst composition from about 0.001% by weight to about 100% by weight based on ethylene are satisfactory with amounts from about 0.01% by weight to about 25% by weight on the same basis being preferred. The ethylene is contacted with the catalyst composition or the catalyst precursor components in the liquid phase in the absence or presence of reaction solvent or diluent which is liquid at reaction temperature and pressure. Illustrative of suitable diluents and solvents are aromatic compounds such as benzene, toluene, chlorobenzene and oxygenated hydrocarbons such as dialkyl ketones, e.g. acetone, methylethyl ketone and ethyl butyl ketone; cycloalkyl ethers, e.g., dioxane, tetrahydrofuran and tetrahydropyran; and acylic alkyl ethers, e.g. dimethoxyethane, diethylene glycol, dimethyl ether and dibutyl ether. Other suitable solvents or diluents include nitriles such as acetonitrile and propionitrile; dialkylamides such as dimethylformamide; and dialkylsulfoxides such as dimethylsulfoxide. Still other suitable solvents or diluents comprise water or water containing a portion of a polar organic co-solvent. Alkanes and alkenes, including cycloalkanes and cycloalkenes, of from 5 to 20 carbon atoms such as butene-1, isopentane, pentene, cyclopentane, cyclohexane, isohexane, heptane, isooctane, decane, decene-1, dodecane, hexadecene and eicosane are also suitable reaction solvents. In some modifications of the oligomerization process, a portion of the product suitably serves as reaction diluent and no added diluent is employed. When diluent is utilized, however, amounts up to about 30 moles of diluent per mole of ethylene are satisfactory. Preferred reaction diluents and solvents are aromatic hydrocarbons, lower dialkylsulfoxides, lower nitriles, alkanes, or mixtures thereof.

Other preferred reaction diluents and solvents are polar organic solvents particularly oxygenated organic solvents. Especially preferred are alkanediols of 4 to 6 carbon atoms, e.g. 1,4-butanediol and 2,5-hexanediol.

Polar organic solvents and diluents are preferred for use in the process in part because the ethylene polymerization product mixture is essentially insoluble in such solvents and diluents. For example, when a polar organic solvent such as an alkanediol is employed, a two phase reaction mixture is formed, i.e., one phase comprising the ethylene oligomerization product mixture, i.e., the alpha-olefins, and a second phase comprising the nickel catalyst and the reaction diluent or solvent. Where a two phase reaction is formed, the ethylene polymerization product phase is utilized for further ethylene oligomerization.

The process is suitably conducted in an inert reaction environment so that the presence of reactive materials such as oxygen is desirably avoided. Reaction conditions are therefore substantially oxygen-free.

The precise method of establishing ethylene/catalyst contact is not critical. In one modification, the catalyst composition and the diluent are charged to an autoclave or similar pressure reactor, the ethylene feed is introduced, and the reaction mixture is maintained with agitation at reaction temperature and pressure for the desired reaction period. Another modification comprises passing, in a continuous manner, the ethylene reactant in liquid phase solution in the reaction diluent through a reaction zone in which a supported catalyst composition is maintained. By any modification, the oligomerization process is conducted at moderate temperatures and pressures. Suitable reaction temperatures vary from about 10° to 250° C., but preferably from 50° C. to 150° C. The reaction is conducted at or above atmospheric pressure. The precise pressure is not critical, so long as the reaction mixture is maintained substantially in a non-gaseous phase. Typical pressures vary from about atmospheric to 5000 psig with the range from about 100 psig to 2000 psig being preferred.

The products are separated and recovered from the reaction mixture by conventional methods such as fractional distillation, selective extraction, filtration, adsorption, and the like. In certain modifications of the process wherein the ethylene oligomerization product is insoluble in the reaction diluent or solvent, e.g., when a polar diluent or solvent is employed and a two phase reaction mixture is formed, the ethylene oligomerization product phase is separated and the catalyst-containing diluent or solvent phase is recycled for further utilization.

During the oligomerization process ethylene is converted to dimer, trimer tetramer, and like oligomers as well as polymers, i.e., polyethylene. The oligomer products are characterized by a high proportion (greater than about 70%) with high linearity (greater than about 70%) of linear terminal olefins and the polyethylene products are characterized by high linearity (greater than about 70%) and crystallinity. The particular product composition generally depends upon the catalyst employed, the solvent employed, the reaction conditions, particularly reaction temperatures and diluent and whether the catalyst is used in the homogeneous or heterogeneous state. These conditions can readily be determined by one skilled in the art.

The ethylene oligomer products are materials of established utility and many are chemicals of commerce. The products are converted by conventional catalysts to the corresponding alcohols. Alternatively the product olefins are converted to secondary alcohols by sulfuric acid-catalyzed hydration.

The instant invention will be illustrated by the following illustrative embodiments which are provided for illustration only and are not to be construed as limiting the invention.

Illustrative Embodiments

The following example illustrates a typical preparation of the catalyst and its use in an oligomerization process.

Bis-(1,5-cyclooctadiene nickel) (0.55 g., 2.0 mmoles.) was dissolved in a suitable solvent (30 ml.) (e.g. benzene, chlorobenzene, dimethylacetamide) and was treated with 0.56 g. (2.0 mmoles) of orthodiphenylphosphinophenol, in a small (85 ml capacity) autoclave, under an inert atmosphere. The autoclave was attached to a manifold and ethylene was introduced. When sufficient ethylene had been added, (usually 4–5 g), the addition was stopped and the autoclave was brought to reaction temperature (usually 70°–80° C.). The solution in the vessel was stirred throughout these operations.

The above was repeated using benzene as a solvent and either the diphenyl-, the diethylphosphinophenol ligand or the o-diphenylphosphinophenyl-methyl ether and toluene as a solvent. The results are shown in Table 1. The difference in conversions based on feed and based on oligomer are presumed to be attributable to higher oligomer (polymer) production.

TABLE 1

ETHYLENE OLIGOMERIZATION/
POLYMERIZATION WITH NICKEL CATALYSTS

Conditions: 2 mmoles $(C_8H_{12})_2Ni$, 2 mmoles ligand, 30 ml benzene 2–5 g ethylene, 55–75° C., 16 hours

| Ligand | $P(C_6H_5)_2$ / OH | $P(C_2H_5)_2$ / OH | *$P(C_6H_5)_2$ / $OCH_3$ |
|---|---|---|---|
| % Conversion Basis | | | |
| Feed | 95 | 3.5 | 5.9 |
| Oligomers | 8.8 | 4.6 | 3.4 |
| % Selectivity | | | |
| $C_4$ | 3.4 | 68 | 5.4 |
| $C_6$ | 12 | 24 | 29 |
| $C_8$ | 15 | 4.3 | 15 |
| $C_{10}$ | 15 | 2.1 | 16 |
| $C_{12}$ | 15 | 0.8 | 11 |

TABLE 1-continued
ETHYLENE OLIGOMERIZATION/POLYMERIZATION WITH NICKEL CATALYSTS Conditions: 2 mmoles $(C_8H_{12})_2Ni$, 2 mmoles ligand, 30 ml benzene 2–5 g ethylene, 55–75° C., 16 hours

| Ligand | $P(C_6H_5)_2$ / OH | $P(C_2H_5)_2$ / OH | *$P(C_6H_5)_2$ / $OCH_3$ |
|---|---|---|---|
| $C_{14}+$ | 40 | 1.2 | 26 |
| % Linearity | | | |
| $C_4$ | 98 | 99 | 100 |
| $C_6$ | 97 | 94 | 93 |
| $C_8$ | 96 | 84 | 93 |
| $C_{10}$ | 96 | — | — |
| $C_{12}$ | 92 | — | — |
| $C_{14}$ | 94 | — | — |

*A separate run for 6 hours provided a linearity of - 100%.

The above experiment is repeated using three different solvents. The results are shown in Table 2 below.

TABLE 2
ETHYLENE OLIGOMERIZATION/POLYMERIZATION WITH $(COD)_2Ni/o-Ph_2PC_6H_4OH$

Conditions: 2 mmoles $(C_8H_{12})_2Ni$, 2 mmoles $o-Ph_2PC_6H_4OH$ 30 cc solvent, 3.5–5.0 g ethylene, 1 hr. reaction time

| Experiment | A[a] | B | C | D | E[a] |
|---|---|---|---|---|---|
| Temp. (°C.) | 62–81 | 70–77 | 86–88 | 77–79 | 73–77 |
| Solvent | Benzene | Benzene | Benzene | $C_6H_5Cl$ | $CH_2Cl_2$ |
| % Conversion Basis | | | | | |
| Feed | 95 | 96 | 95 | 97 | 3.9 |
| Olig. | 8.8 | 2.7 | 20 | 3.6 | 3.3 |
| % Selectivity | | | | | |
| $C_4$ | 3.4 | 2.5 | 3.4 | 5.1 | 9.9 |
| $C_6$ | 12 | 6.6 | 10 | 5.0 | 18 |
| $C_8$ | 15 | 12 | 13 | 7.2 | 19 |
| $C_{10+}$ | 70 | 69 | 73 | 83 | 52 |
| % Linearity | | | | | |
| $C_4$ | 98 | 100 | 100 | 100 | 95 |
| $C_6$ | 97 | 100 | 100 | 100 | 100 |
| $C_8$ | 96 | 100 | 100 | 100 | 100 |
| $C_{10}$ | 96 | 100 | 97 | 100 | 84 |
| % α-olefins | | | | | |
| $C_4$ | — | — | 88 | 99 | 43 |
| $C_6$ | — | — | 86 | 100 | 40 |
| $C_8$ | — | — | 86 | 94 | 35 |
| $C_{10}$ | — | — | 95 | 87 | 55 |

[a]Reaction time: 16 hours.

The above example was repeated using 0.55 grams of bis-(1,5-cyclooctadiene nickel), 0.56 grams of diphenylphosphinophenol and 30 cubic centimeters of dimethylacetamide. 1.9 grams of ethylene were charged to the reactor. The reaction temperature ranged from about 45° to about 75° C. and reaction pressure ranged from about 250–1000 psig. After about 1½ hours the reaction was terminated. The reaction products were analyzed and the results are shown in Table 3.

TABLE 3
OLIGOMER PRODUCT DISTRIBUTION

| Product | % Selectivity | % Linearity | % α-olefins | K[a] |
|---|---|---|---|---|
| $C_4$ | 3.6 | 100 | 98 | 0.91 |
| $C_6$ | 4.9 | 100 | 97 | 1.24 |
| $C_8$ | 8.1 | 100 | 86 | 1.03 |
| $C_{10}$ | 10.4 | 100 | 96 | 0.83 |
| $C_{12}$ | 10.3 | 100 | 96 | 1.02 |
| $C_{14}$ | 12.3 | 100 | 98 | 0.82 |
| $C_{16}$ | 11.5 | 100 | 93 | 0.89 |
| $C_{18}$ | 11.5 | 100 | 87 | 0.84 |
| $C_{20}$ | 10.7 | 100 | 90 | 0.71 |
| $C_{22}$ | 8.4 | 100 | 100 | 0.87 |
| $C_{24}$ | 8.0 | — | — | |
| $C_{26+}$ | | | | |

[a]$K = \dfrac{C_{n+2}}{C_n}$

A sample of polymer removed from the reactor of experiment A in Table 2 above was analyzed and determined to be polyethylene with the following characteristics.

By Differential scanning calorimetry:
M.P.   115.5° C. (heating scan)
       109.0° C. (cooling scan)

By Gel Permeation chromatography:
Mn (number average molecular wt.) = 1097
Mw (weight average molecular wt.) = 2161 Bimodal molecular wt distribution
$M_Z$ (Z average) = 8127
Q = 1.27

I claim:

1. A catalyst composition which comprises the product of reacting in liquid phase solution at a temperature of from about 25° C. to 100° C. a nickel compound represented by a formula selected from the group consisting of

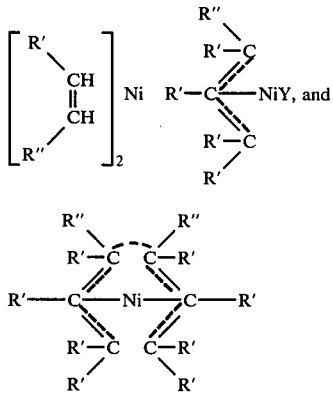

wherein R" and R' independently are hydrogen, alkyl, cycloalkyl, alkenyl, cycloalkenyl, aralkyl, aryl or alkaryl of up to 8 carbon atoms and Y is halogen of atomic number 17 to 53 inclusive, alkoxy or alkanoyloxy of up to 10 carbon atoms with the proviso that R" together with R' may form a divalent hydrocarbyl moiety of 2 to 10 carbon atoms and of up to three additional olefinic double bonds, with a dihydrocarbylphosphinophenyl alcohol or lowr alkyl ether ligand, the molar ratio of nickel compound to ligand being from about 0.5:1 to 1:12.

2. The composition of claim 1 wherein the ligand is o-diarylphosphinophenol.

3. The composition of claim 2 wherein the ligand is o-diphenylphosphinophenol.

4. The composition of claim 1 wherein the ligand is o-diphenylphosphinophenyl methyl ether.

5. The composition of claim 1 in which said reaction of said nickel compound with said ligand is carried out in the present of ethylene.

6. The composition of claim 1 in which said nickel compound is biscyclooctadiene-1,5-nickel (O).

7. A process for preparing a catalyst composition which comprises contacting in liquid phase solution at a temperature of from about 25° C. to 100° C. a nickel compound represented by a formula selected from the group consisting of:

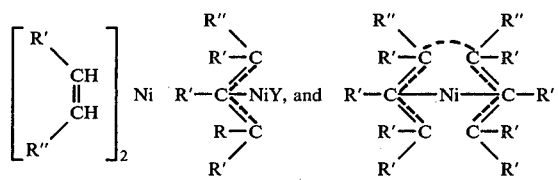

wherein R" and R' independently are hydrogen, alkyl, cycloalkyl, alkenyl, cycloalkenyl, aralkyl, aryl or alkaryl of up to 8 carbon atoms and Y is halogen of atomic number 17 to 53 inclusive, alkoxy or alkanoyloxy of up to 10 carbon atoms with the proviso that R" together with one R' may form a divalent hydrocarbyl moiety of 2 to 10 carbon atoms and of up to three additional olefinic double bonds, with a dihydrocarbylphosphinophenyl alcohol or lower alkyl ether ligand, the molar ratio of nickel compound to ligand being from about 0.5:1 to 1:12.

8. The process of claim 7 wherein said contacting is carried out in the presence of ethylene.

9. The process of claim 7 in which said nickel compound is reacted with said ligand in a molar ratio of nickel compound to acid of from about 1:1 to 1:4.

10. The process of claim 7 wherein said ligand is o-diarylphosphinophenol.

11. The process of claim 10 wherein said ligand is o-diphenylphosphinophenyl alcohol.

12. The process of claim 7 in which said nickel compound is biscyclooctadiene-1,5-nickel (O).

13. The process of claim 7 wherein said ligand is o-diphenylphosphinophenyl methyl ether.

* * * * *